US005385959A

United States Patent [19]

Tsaur et al.

[11] Patent Number: 5,385,959

[45] Date of Patent: Jan. 31, 1995

[54] CAPSULE WHICH COMPRISES A COMPONENT SUBJECT TO DEGRADATION AND A COMPOSITE POLYMER

[75] Inventors: Liang S. Tsaur, Norwood, N.J.; Michael P. Aronson, West Nyack, N.Y.

[73] Assignee: Lever Brothers Company, Division of Conopco, Inc., New York, N.Y.

[21] Appl. No.: 36,766

[22] Filed: Mar. 25, 1993

Related U.S. Application Data

[63] Continuation-in-part of Ser. No. 875,914, Apr. 29, 1992, abandoned.

[51] Int. Cl.[6] ...................... C08L 89/00; C11D 17/08; C12N 9/96; B32B 9/02

[52] U.S. Cl. ...................................... 523/201; 252/90; 252/174.12; 252/174.13; 428/402.24; 435/188; 524/17; 524/20; 525/902; 523/202; 523/205; 523/207; 523/210

[58] Field of Search .................... 524/17, 20; 523/201, 523/205, 206, 207, 202, 210, 211; 525/902; 435/188; 252/174.12, 174.13, 90; 428/402.24

[56] References Cited

U.S. PATENT DOCUMENTS

| | | | |
|---|---|---|---|
| 3,996,156 | 12/1976 | Matsukawa et al. | 264/4.7 |
| 4,115,474 | 9/1978 | Vasillades | 524/55 |
| 4,749,501 | 2/1980 | Nakagawa et al. | 252/117 |
| 4,759,956 | 7/1988 | Amer et al. | 252/174.13 |
| 4,777,089 | 10/1988 | Takizawa et al. | 428/402.22 |
| 4,829,101 | 5/1989 | Kraemer et al. | 523/201 |
| 4,842,761 | 6/1989 | Rutherford | 523/102 |
| 4,898,781 | 2/1990 | Onouchi et al. | 428/402.22 |
| 4,906,396 | 3/1990 | Falholt et al. | 252/174.12 |
| 4,908,233 | 3/1990 | Takizawa et al. | 428/402.22 |
| 4,973,417 | 11/1990 | Falholt | 252/174.12 |
| 5,059,341 | 10/1991 | Holmes | 252/174.12 |
| 5,147,576 | 9/1992 | Montague | 252/174 |
| 5,198,353 | 3/1993 | Hawkins et al. | 252/174.12 |

FOREIGN PATENT DOCUMENTS

| | | |
|---|---|---|
| 266796 | of 0000 | European Pat. Off. . |
| 351162 | of 0000 | European Pat. Off. . |
| 1390503 | of 0000 | European Pat. Off. . |

*Primary Examiner*—Peter Szekely
*Attorney, Agent, or Firm*—Ronald A. Koatz

[57] ABSTRACT

The present invention relates to a capsule for use in heavy duty liquid compositions which capsule comprises:

(1) a component subject to degradative attack; and (2) a composite polymer which in turn comprises a hydrophilic portion and hydrophobic polymer core particle.

3 Claims, No Drawings

CAPSULE WHICH COMPRISES A COMPONENT SUBJECT TO DEGRADATION AND A COMPOSITE POLYMER

This application is a continuation-in-part of 07/875,914 filed Apr. 29, 1992, now abandoned.

BACKGROUND OF THE INVENTION

1. Field of the Invention

The present invention relates to capsules for use in heavy duty liquid detergent compositions which capsules comprise (1) a component subject to degradation; and (2) a novel composite polymer comprising hydrophobic particles and hydrophilic polymers attached thereto wherein the sensitive component is entrapped within the composite polymer.

2. Prior Art

It is well known in the art that heavy duty liquid detergents provide a hostile environment for desirable ingredients such as, for example, bleaches, enzymes and perfumes. It is therefore often desirable to protect a sensitive component such as an enzyme from the composition during storage yet ensure its release in a controlled and reproducible manner when the liquid is used by consumers. In this manner, components which are sensitive to the ingredients found in the compositions (e.g., enzymes in detergent compositions, particularly concentrated detergent compositions, are denatured by surfactants in the detergent composition) can be encapsulated and protected until they are ready for release; or other components which are simply more desirably released later in the wash (e.g., perfumes or anti-foams) can be controllably released, for example, by dilution of a concentrated liquid.

In particular, it is desirable to encapsulate one or more enzymes since enzymes are highly efficient laundry washing ingredients used to promote removal of soils and stains during the cleaning process.

European Patent Application No. 266,796 (assigned to Showa Denko), for example, teaches water-soluble microcapsules comprising an enzyme, preferably dissolved or dispersed in a water containing polyhydroxy compound, and coated with a water soluble polyvinyl alcohol (PVA) or partially hydrolyzed polyvinyl alcohol as the coating material. There is no teaching or suggestion of composite polymer comprising a network formed by hydrophobic particles to which are chemically or physically attached hydrophilic polymers and in which system or network enzyme or other sensitive component is entrapped. In addition, the PVA used in the Showa Denko reference, in contrast to the PVA which could be used as a hydrophilic component of the subject invention, has an average degree of polymerization in the range of 200–3000 and a percent hydrolysis not less than 90%, preferably not less than 95%. It is said that if the percent hydrolysis of PVA is lower than 90%, the microcapsule is not stable and will dissolve during storage in a water-containing liquid detergent. This is probably not surprising in that there is nothing to stabilize the capsule other than a cross-linking agent, i.e., there is no teaching or suggestion of hydrophobic core particles comprising an ethylenically unsaturated group to which the hydrophilic polymers can affix, chemically or physically, to form an entrapping network.

That is, the encapsulating polymer of this reference comprises only the use of a water soluble polymer (i.e., PVA) rather than an entrapping polymer which is a composite emulsion copolymer comprising both water-soluble (i.e., hydrophilic attaching polymer) and water insoluble (i.e., hydrophobic particles to which hydrophilic polymers attach) components or domains. The use of a totally water soluble polymer does not provide optimal resistance to water such polymers are also more difficult to process than the composite polymers of this invention. Finally, at the levels of hydrolysis for PVA taught in this reference (i.e. greater than 90%, preferably greater than 95%), it is difficult to dissolve the capsule or polymer at ambient temperatures and the protected component is only partly released upon dilution. Moreover, the reference does not allow the option of using less hydrolyzed PVA because, although the less hydrolyzed PVA will dissolve more readily when diluted, such a PVA is too water sensitive and would fail to protect the component during storage.

U.S. Pat. No. 4,906,396 to Falholt et al. teaches an enzyme dispersed in a hydrophobic substance. Again, there is no teaching or suggestion of a polymer which is a composite emulsion copolymer comprising both water soluble and water insoluble components.

EP 1,390,503 (assigned to Unilever) teaches a polymer which dissolves when the ionic strength of the liquid decreases upon dilution. Further, there is no teaching of a polymer system comprising a composite emulsion polymer which in turn comprises a hydrophilic portion (i.e., hydrophilic polymer or polymers) chemically and/or physically attached to a hydrophobic core portion (i.e., hydrophobic particles) to form an entrapping emulsion polymer in which the enzyme component is trapped.

Takizawa et al. (U.S. Pat. Nos. 4,777,089 & 4,908,233) teach the use of a microcapsule which comprises a "core" material (i.e., the protected material is the core) coated with a single water soluble polymer (which polymer undergoes phase separation by the action of an electrolyte in the compositions). Again, there is no teaching or suggestion of a composite emulsion polymer comprising a hydrophilic portion chemically or physically attached to hydrophobic core particles and used to entrap sensitive materials subject to degradation. Such a composite polymer having both a hydrophilic and hydrophobic portion offers significant advantages over the solely water-soluble encapsulating polymers of the reference in that it entraps the component and slows migration of harsh components from outside the capsule to the sensitive component as well as slows migration of the sensitive component to water and harsh components outside the capsule.

U.S. Pat. No. 4,842,761 to Rutherford teaches compositions and methods for controlled release of fragrance-bearing substances (perfumes) wherein the compositions comprise a water-soluble and a water-insoluble (both normally solid) polymer and a perfume composition, a portion of the perfume composition being incorporated in the water-soluble polymer and a portion incorporated in the water-insoluble polymer. The two polymers are physically associated with each other in such a manner that one is in the form of discrete entities in a matrix of the other. The particles of this reference have a particle size of between 100–3000 microns in contrast to the capsules of the invention which have a particle size of under 100 microns. In addition, the capsules are formed by intermixing water soluble and water insoluble polymer under high shear resulting in a different capsule system than the emulsion polymer capsule of the subject invention.

Applicants co-pending U.S. Ser. No. 07/766,477 now U.S. Pat No. 5,296,977 teaches a water soluble polymer used to encapsulate particles made of an emulsifiable mixture of a fragrance and a wax. The waxes used are hydrocarbons such as paraffin wax and microcrystalline wax. These waxes differ from the core hydrophobic particles of the invention. Moreover, the core is not simply a wax material enveloping the perfume but an intimate mixture of the wax and perfume which differs completely from the core particles of the subject invention which may stand alone. In fact, the enzymes of the subject invention are not inside the hydrophobic core particles at all. Finally, the encapsulated material of the reference is released by heat trigger whereas the material of the invention is dilution triggered.

U.S. Pat. No. 4,115,474 to Vassiliades discloses a hydroxy containing polymer shell be grafted onto a water insoluble core. They hydroxy shell is cross-linked with a formaldehyde condensation product and will chloroform not release upon dilution by water. Moreover, the reference has not even refer to entrapped sensitive materials which can be released. Indeed, the capsule is intended to be a load bearing capsule which is not even subject to pressure release.

None of these patents teach capsules comprising the specific composite emulsion polymers of the invention which are intended for dilution release of entrapped sensitive materials.

Thus, there is a need in the art for capsules for use in heavy duty liquid compositions wherein said capsules comprise novel composite polymers which can both stabilize components subject to degradative attack and yet readily break down to release the component in use (e.g., in diluted aqueous medium, especially at ambient temperatures).

Accordingly, it is an object of this invention to provide such a novel composite polymer that can stabilize and isolate sensitive ingredients in heavy duty liquid compositions while simultaneously being able to deliver the ingredients in a controlled and reproducible manner when the composition is diluted with water during use.

SUMMARY OF THE INVENTION

The present invention provides a capsule for use in heavy duty liquid compositions which capsule comprises (1) a component or components normally subject to degradation by components in heavy duty liquid compositions; and (2) a composite polymer forming a network in which the component(s) are released upon dilution of the concentrated liquids.

Specifically the composite emulsion copolymer in turn comprises a hydrophilic portion (i.e., hydrophilic polymer attaching to the hydrophobic particles) and a hydrophobic polymer core (i.e., particles to which hydrophilic polymers attach) portion wherein the hydrophilic portion comprises hydrophilic (preferably crosslinkable) water soluble polymer or polymers physically or chemically attached to said hydrophobic polymer particles. The emulsion copolymer forms a network which entraps enzymes or other sensitive components between the hydrophobic particles and preferably cross-linked water soluble polymers and, it is believed, thereby acts like a form of gel and slows the migration of the sensitive component out of the capsule as well as the flow degradative components from outside the capsule to the sensitive component trapped therein.

DETAILED DESCRIPTION OF THE INVENTION

The present invention provides a capsule for use in heavy duty liquid compositions which capsule comprises:

(1) a component or components normally subject to degradation in such compositions; and (2) a composite polymer which comprises hydrophobic core particles and hydrophilic polymers attached thereto wherein the sensitive component is entrapped within the network formed by the composite polymer.

The composite emulsion polymer comprises a hydrophilic, preferably cross-linkable, water soluble component or components attached (via physical entanglement or chemical attachment) onto hydrophobic polymer particles which form the "cores" of the emulsion polymer. Some percentage of hydrophilic polymers may remain free and do not attach. Enzymes or other sensitive components are entrapped in the web formed by the hydrophilic polymers attached to the hydrophobic particles and/or crosslinked with each other.

Compositions

The various components of heavy duty liquid (HDL) compositions in which the capsules of the invention may be used are set forth in greater detail below.

Detergent Active

The compositions contain one or more surface active agents selected from the group consisting of anionic, nonionic, cationic, ampholytic and zwitterionic surfactants or mixtures thereof. The preferred surfactant detergents are mixtures of anionic and nonionic surfactants although it is to be understood that any surfactant may be used alone or in combination with any other surfactant or surfactants.

Anionic Surfactant Detergents

Anionic surface active agents which may be used are those surface active compounds which contain a long chain hydrocarbon hydrophobic group in their molecular structure and a hydrophile group, i.e. water solubilizing group such as sulfonate or sulfate group. The anionic surface active agents include the alkali metal (e.g. sodium and potassium) water soluble higher alkyl benzene sulfonates, alkyl sulfonates, alkyl sulfates and the alkyl poly ether sulfates. They may also include fatty acids or fatty acid soaps. The preferred anionic surface active agents are the alkali metal, ammonium or alkanolamide salts of higher alkyl benzene sulfonates and alkali metal, ammonium or alkanolamide salts of higher alkyl sulfonates. Preferred higher alkyl sulfonate are those in which the alkyl groups contain 8 to 26 carbon atoms, preferably 12 to 22 carbon atoms and more preferably 14 to 18 carbon atoms. The alkyl group in the alkyl benzene sulfonate preferably contains 8 to 16 carbon atoms and more preferably 10 to 15 carbon atoms. A particularly preferred alkyl benzene sulfonate is the sodium or potassium dodecyl benzene sulfonate, e.g. sodium linear dodecyl benzene sulfonate. The primary and secondary alkyl sulfonates can be made by reacting long chain alpha-olefins with sulfites or bisulfites, e.g. sodium bisulfite. The alkyl sulfonates can also be made by reacting long chain normal paraffin hydrocarbons with sulfur dioxide and oxygen as describe in U.S. Pat. Nos. 2,503,280, 2,507,088, 3,372,188 and 3,260,741 to obtain normal or secondary higher alkyl sulfonates suitable for use as surfactant detergents.

The alkyl substituent is preferably linear, i.e. normal alkyl, however, branched chain alkyl sulfonates can be employed, although they are not as good with respect to biodegradability. The alkane, i.e. alkyl, substituent may be terminally sulfonated or may be joined, for example, to the 2-carbon atom of the chain, i.e. may be a secondary sulfonate. It is understood in the art that the substituent may be joined to any carbon on the alkyl chain. The higher alkyl sulfonates can be used as the alkali metal salts, such as sodium and potassium. The preferred salts are the sodium salts. The preferred alkyl sulfonates are the $C_{10}$ to $C_{18}$ primary normal alkyl sodium and potassium sulfonates, with the $C_{10}$ to $C_{15}$ primary normal alkyl sulfonate salt being more preferred.

Mixtures of higher alkyl benzene sulfonates and higher alkyl sulfonates can be used as well as mixtures of higher alkyl benzene sulfonates and higher alkyl polyether sulfates.

The alkali metal alkyl benzene sulfonate can be used in an amount of 0 to 70%, preferably 10 to 50% and more preferably 10 to 20% by weight.

The alkali metal sulfonate can be used in admixture with the alkylbenzene sulfonate in an amount of 0 to 70%, preferably 10 to 50% by weight.

Also normal alkyl and branched chain alkyl sulfates (e.g., primary alkyl sulfates) may be used as the anionic component).

The higher alkyl polyether sulfates used can be normal or branched chain alkyl and contain lower alkoxy groups which can contain two or three carbon atoms. The normal higher alkyl polyether sulfates are preferred in that they have a higher degree of biodegradability than the branched chain alkyl and the lower poly alkoxy groups are preferably ethoxy groups.

The preferred higher alkyl poly ethoxy sulfates used in accordance with the present invention are represented by the formula:

$$R^1—O(CH_2CH_2O)_p—SO_3M,$$

where $R^1$ is $C_8$ to $C_{20}$ alkyl, preferably $C_{10}$ to $C_{18}$ and more preferably $C_{12}$ to $C_{15}$; p is 2 to 8, preferably 2 to 6, and more preferably 2 to 4; and M is an alkali metal, such as sodium and potassium, or an ammonium cation. The sodium and potassium salts are preferred.

A preferred higher alkyl poly ethoxylated sulfate is the sodium salt of a triethoxy $C_{12}$ to $C_{15}$ alcohol sulfate having the formula:

$$C_{12-15}—O—(CH_2CH_2O)_3—SO_3Na$$

Examples of suitable alkyl ethoxy sulfates that can be used are $C_{12-15}$ normal or primary alkyl triethoxy sulfate, sodium salt; n-decyl diethoxy sulfate, sodium salt; $C_{12}$ primary alkyl diethoxy sulfate, ammonium salt; $C_{12}$ primary alkyl triethoxy sulfate, sodium salt: $C_{15}$ primary alkyl tetraethoxy sulfate, sodium salt, mixed $C_{14-15}$ normal primary alkyl mixed tri- and tetraethoxy sulfate, sodium salt; stearyl pentaethoxy sulfate, sodium salt; and mixed $C_{10-18}$ normal primary alkyl triethoxy sulfate, potassium salt.

The normal alkyl ethoxy sulfates are readily biodegradable and are preferred. The alkyl poly-lower alkoxy sulfates can be used in mixtures with each other and/or in mixtures with the above discussed higher alkyl benzene, alkyl sulfonates, or alkyl sulfates.

The alkali metal higher alkyl poly ethoxy sulfate can be used with the alkylbenzene sulfonate and/or with an alkyl sulfonate or sulfonate, in an amount of 0 to 70%, preferably 10 to 50% and more preferably 10 to 20% by weight of entire composition.

Nonionic Surfactant

Nonionic synthetic organic detergents which can be used alone or in combination with other surfactants are described below.

As is well known, the nonionic detergents are characterized by the presence of an organic hydrophobic group and an organic hydrophilic group and are typically produced by the condensation of an organic aliphatic or alkyl aromatic hydrophobic compound with ethylene oxide (hydrophilic in nature). Typical suitable nonionic surfactants are those disclosed in U.S. Pat. Nos. 4,316,812 and 3,630,929.

Usually, the nonionic detergents are polyalkoxylated lipophiles wherein the desired hydrophile-lipophile balance is obtained from addition of a hydrophilic poly-lower alkoxy group to a lipophilic moiety. A preferred class of nonionic detergent is the alkoxylated alkanols wherein the alkanol is of 9 to 18 carbon atoms and wherein the number of moles of alkylene oxide (of 2 or 3 carbon atoms) is from 3 to 12. Of such materials it is preferred to employ those wherein the alkanol is a fatty alcohol of 9 to 11 or 12 to 15 carbon atoms and which contain from 5 to 8 or 5 to 9 alkoxy groups per mole.

Exemplary of such compounds are those wherein the alkanol is of 12 to 15 carbon atoms and which contain about 7 ethylene oxide groups per mole, e.g. Neodol 25-7 and Neodol 23-6.5, which products are made by Shell Chemical Company, Inc. The former is a condensation product of a mixture of higher fatty alcohols averaging about 12 to 15 carbon atoms, with about 7 moles of ethylene oxide and the latter is a corresponding mixture wherein the carbon atoms content of the higher fatty alcohol is 12 to 13 and the number of ethylene oxide groups present averages about 6.5. The higher alcohols are primary alkanols.

Other useful nonionics are represented by the commercially well known class of nonionics sold under the trademark Plurafac. The Plurafacs are the reaction products of a higher linear alcohol and a mixture of ethylene and propylene oxides, containing a mixed chain of ethylene oxide and propylene oxide, terminated by a hydroxyl group. Examples include $C_{13}$–$C_{15}$ fatty alcohol condensed with 6 moles ethylene oxide and 3 moles propylene oxide, $C_{13}$–$C_{15}$ fatty alcohol condensed with 7 moles propylene oxide and 4 moles ethylene oxide, $C_{13}$–$C_{15}$ fatty alcohol condensed with 5 moles propylene oxide and 10 moles ethylene oxide or mixtures of any of the above.

Another group of liquid nonionics are commercially available from Shell Chemical Company, Inc. under the Dobanol trademark: Dobanol 91-5 is an ethoxylated $C_9$–$C_{11}$ fatty alcohol with an average of 5 moles ethylene oxide and Dobanol 25-7 is an ethoxylated $C_{12}$–$C_{15}$ fatty alcohol with an average of 7 moles ethylene oxide per mole of fatty alcohol.

Preferred nonionic surfactants include the $C_{12}$–$C_{15}$ primary fatty alcohols with relatively narrow contents of ethylene oxide in the range of from about 7 to 9 moles, and the $C_9$ to $C_{11}$ fatty alcohols ethoxylated with about 5–6 moles ethylene oxide.

Another class of nonionic surfactants which can be used are glycoside surfactants. Glycoside surfactants suitable for use include those of the formula:

$$RO-R^1O-_y(Z)_x$$

wherein R is a monovalent organic radical containing from about 6 to about 30 (preferably from about 8 to about 18) carbon atoms; $R^1$ is a divalent hydrocarbon radical containing from about 2 to 4 carbons atoms; 0 is an oxygen atom; y is a number which can have an average value of from 0 to about 12 but which is most preferably zero; Z is a moiety derived from a reducing saccharide containing 5 or 6 carbon atoms; and x is a number having an average value of from 1 to about 10 (preferably from about 1½ to about 10).

A particularly preferred group of glycoside surfactants includes those of the formula above in which R is a monovalent organic radical (linear or branched) containing from about 6 to about 18 (especially from about 8 to about 18) carbon atoms; y is zero; z is glucose or a moiety derived therefrom; x is a number having an average value of from 1 to about 4 (preferably from about 1½ to 4).

Mixtures of two or more of the nonionic surfactants can be used.

Cationic Surfactants

Many cationic surfactants are known in the art, and almost any cationic surfactant having at least one long chain alkyl group of about 10 to 24 carbon atoms is suitable in the present invention. Such compounds are described in "Cationic Surfactants", Jungermann, 1970, incorporated by reference.

Specific cationic surfactants which can be used are described in detail in U.S. Pat. No. 4,497,718, hereby incorporated by reference.

As with the nonionic and anionic surfactants, the compositions may use cationic surfactants alone or in combination with any of the other surfactants known in the art. Of course, the compositions may contain no cationic surfactants at all.

Amphoteric Surfactants

Ampholytic synthetic detergents can be broadly described as derivatives of aliphatic or aliphatic derivatives of heterocyclic secondary and tertiary amines in which the aliphatic radical may be straight chain or branched and wherein one of the aliphatic substituents contains from about 8 to 18 carbon atoms and at least one contains an anionic water-solubilizing group, e.g. carboxy, sulfonate,sulfate. Examples of compounds falling within this definition are sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyldodecylamino)propane 1-sulfonate, disodium octadecyl-imminodiacetate, sodium 1-carboxymethyl-2-undecylimidazole, and sodium N,N-bis(2-hydroxyethyl)-2-sulfato-3-dodecoxypropylamine. Sodium 3-(dodecylamino)propane-1-sulfonate is preferred.

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. The cationic atom in the quaternary compound can be part of a heterocyclic ring. In all of these compounds there is at least one aliphatic group, straight chain or branched, containing from about 3 to 18 carbon atoms and at least one aliphatic substituent containing an anionic water-solubilizing group, e.g., carboxy, sulfonate, sulfate, phosphate, or phosphonate.

Specific examples of zwitterionic surfactants which may be used are set forth in U.S. Pat. No. 4,062,647, hereby incorporated by reference.

The amount of active used may vary from 1 to 85% by weight, preferably 10 to 50% by weight.

It should be noted that the compositions in which the capsules of the invention are used may be structured or unstructured.

By structured liquid composition is meant a composition in which at least some of the detergent active forms a structured phase which is capable of suspending a solid particulate material.

More particularly, when a structured liquid is contemplated, the composition requires sufficient electrolyte to cause the formation of a lamellar phase by the soap/surfactant to endow capability to suspend solids. The selection of the particular type(s) and amount of electrolyte to bring this into being for a given choice of soap/surfactant is effected using methodology very well known to those skilled in the art. It utilizes the particular techniques described in a wide variety of references. One such technique entails conductivity measurements. The detection of the presence of such as lamellar phase is also very well known and may be effected by, for example, optical and electron microscopy or x-ray diffraction, supported by conductivity measurement.

If structured liquids are used, structured surfactant combinations can include, for example, LAS/ethoxylated alcohol, LAS/lauryl ether sulfate (LES), LAS/-LES/ethoxylated alcohol, amine oxide/SDS, coconut ethanolamide/LAS and other combinations yielding lamellar phase liquids.

As indicated above, aqueous surfactant structured liquids are capable of suspending solid particles without the need of other thickening agent and can be obtained by using a single surfactant or mixtures of surfactants in combination with an electrolyte. The liquid so structured contains lamellar droplets in a continuous aqueous phase.

The preparation of surfactant-based suspending liquids is known in the art and normally requires a nonionic and/or an anionic surfactant and an electrolyte, though other types of surfactant or surfactant mixtures such as the cationics and zwitterionics, can also be used.

Builders/Electrolytes

Builders which can be used include conventional alkaline detergency builders, inorganic or organic, which can be used at levels from about 0.5% to about 50% by weight of the composition, preferably from 3% to about 35% by weight. More particularly, when structured compositions are used, preferred amounts of builder are 5%–35% by weight.

As indicated above, a structured liquid is one which requires sufficient electrolyte to cause formation of a lamellar phase by the soap/surfactant to endow solid suspending capability.

As used herein, the term electrolyte means any water-soluble salt.

If a structured composition is desired, the amount of electrolyte used should be sufficient to cause formation of a lamellar phase by the soap/surfactant to endow solid suspending capability. Preferably the composition comprises at least 1.0% by weight, more preferably at least 5.0% by weight, most preferably at least 10.0% by weight of electrolyte. The electrolyte may also be a detergency builder, such as the inorganic builder sodium tripolyphosphate, or it may be a non-functional electrolyte such as sodium sulphate or chloride. Preferably the inorganic builder comprises all or part of the electrolyte.

It should be noted that, even if the compositions are not electrolyte structured, there should be sufficient electrolyte to stabilize the capsule (described below) in the composition. Thus, the composition, whether structured or not, should comprise at least about 1%, preferably at least about 3%, preferably 3% to as much as about 50% by weight electrolyte.

Structured compositions, if used, are capable of suspending particulate solids, although particularly preferred are those systems where such solids are actually in suspension. The solids may be undissolved electrolyte, the same as or different from the electrolyte in solution, the latter being saturated in electrolyte. Additionally, or alternatively, they may be materials which are substantially insoluble in water alone. Examples of such substantially insoluble materials are aluminosilicate builders and particles of calcite abrasive.

Examples of suitable inorganic alkaline detergency builders which may be used (in structured or unstructured compositions) are water-soluble alkalimetal phosphates, polyphosphates, borates, silicates and also carbonates. Specific examples of such salts are sodium and potassium triphosphates, pyrophosphates, orthophosphates, hexametaphosphates, tetraborates, silicates and carbonates.

Examples of suitable organic alkaline detergency builder salts are: (1) water-soluble amino polycarboxylates, e.g., sodium and potassium ethylenediaminetetraacetates, nitrilotriacetates and N-(2 hydroxyethyl)-nitrilodiacetates; (2) water-soluble salts of phytic acid, e.g., sodium and potassium phytates (see U.S. Pat. No. 2,379,942); (3) water-soluble polyphosphonates, including specifically, sodium, potassium and lithium salts of ethane-1-hydroxy-1,1-diphosphonic acid; sodium, potassium and lithium salts of methylene diphosphonic acid; sodium, potassium and lithium salts of ethylene diphosphonic acid; and sodium, potassium and lithium salts of ethane-1,1,2-triphosphonic acid. Other examples include the alkali metal salts of ethane-2-carboxy-1,1-diphosphonic acid hydroxymethanediphosphonic acid, carboxyldiphosphonic acid, ethane-1-hydroxy-1,1,2-triphosphonic acid, ethane-2-hydroxy-1,1,2-triphosphonic acid, propane-1,1,3,3-tetraphosphonic acid, propane-1,1,2,3-tetraphosphonic acid, and propane-1,2,2,3-tetraphosphonic acid; (4) water-soluble salts of polycarboxylate polymers and copolymers as described in U.S. Pat. No 3,308,067.

In addition, polycarboxylate builders can be used satisfactorily, including water-soluble salts of mellitic acid, citric acid, and carboxymethyloxysuccinic acid, salts of polymers of itaconic acid and maleic acid, tartrate monosuccinate, tartrate disuccinate and mixtures thereof (TMS/TDS).

Certain zeolites or aluminosilicates can be used. One such aluminosilicate which is useful in the compositions of the invention is an amorphous water-insoluble hydrated compound of the formula $Na_x(_yAlO_2.SiO_2)$, wherein x is a number from 1.0 to 1.2 and y is 1, said amorphous material being further characterized by a Mg++ exchange capacity of from about 50 mg e.g. $CaCO_3$/g. and a particle diameter of from about 0.01 micron to about 5 microns. This ion exchange builder is more fully described in British Pat. No. 1,470,250.

A second water-insoluble synthetic aluminosilicate ion exchange material useful herein is crystalline in nature and has the formula $Na_z[(AlO_2)_y.(SiO_2)]xH_2O$, wherein z and y are integers of at least 6; the molar ratio of z to y is in the range from 1.0 to about 0.5, and x is an integer from about 15 to about 264; said aluminosilicate ion exchange material having a particle size diameter from about 0.1 micron to about 100 microns; a calcium ion exchange capacity on an anhydrous basis of at least about 200 milligrams equivalent of $CaCO_3$ hardness per gram; and a calcium exchange rate on an anhydrous basis of at least about 2 grains/gallon/minute/gram. These synthetic aluminosilicates are more fully described in British Pat. No. 1,429,143.

Capsule Polymers

The present invention provides a capsule(s) comprising a sensitive component subject to degradation and a composite polymer as described in greater detail below.

The composite polymer of the capsule may be prepared via the emulsion polymerization of a free radical polymerizable monomer or monomer mixture (i.e., the monomer which will form the core hydrophobic particles to which the hydrophilic polymer or polymers are attached) in the presence of the water soluble polymer or polymers. Preferably more than 20%, more preferably greater than 40% of the water soluble polymer or polymers will attach to the polymeric particles. The remaining polymer remains free although, of course, it can cross-link to further stabilize the capsule.

The particle size of the hydrophobic particles is generally less than 10 microns, preferably less than 1 micron, more preferably less than 0.5 microns in size.

A variety of polar and semi-polar polymers can be used as the hydrophilic polymer or polymers which form the composite emulsion polymers of the present invention. Preferred hydrophilic polymers are those that are or can be made insoluble in the composition in which the encapsulate is employed (preferably, a concentrated liquid composition), yet are capable of interacting with and stabilizing the hydrophobic monomer particle cores derived therefrom during the preparation of the composite polymer. Two broad types of hydrophilic polymers are useful.

The first type is nonionic water soluble polymers that display an upper consulate temperature or cloud point. As is well known in the art (P. Molyneaux, Water Soluble Polymers CRC Press, Boca Raton, 1984), the solubility or cloud point of such polymers is sensitive to electrolyte and can be "salted out" by the appropriate type and level of electrolyte. Such polymers can generally be efficiently salted out by realistic levels of electrolyte (<10%) and also have sufficient hydrophobic groups to interact with hydrophobic monomers such as styrene that will allow formation of high grafted composite particles. Suitable polymers in this class are synthetic nonionic water soluble polymers including: polyvinyl alcohol and its copolymers with vinyl acetate; polyvinyl pyrrolidone and its various copolymers with styrene and vinyl acetate; and polyacrylamide and its various modification such as those discussed by Molyneaux (see above) and McCormick (in Encyclopedia of Polymer Science Vol. 17, John Wiley, New York). Another class of useful polymers are modified polysaccharides such as partially hydrolyzed cellulose acetate, hydroxy ethyl, hydroxy propyl and hydroxybutyl cellulose, methyl cellulose and the like. Proteins and modified proteins such as gelatin are still another class of polymers useful in the present invention especially when selected to have an isoelectric pH close to that of the liquid composition in which the polymers are to be employed.

The second broad type of polymer useful as the hydrophilic polymer which will attach to the hydrophobic polymer core particles (and/or to each other) and form composite emulsion polymers of the instant invention, are those which bear functional groups that can form labile chemical or ionic cross-links with an optional cross-linking agent. By labile cross-links is meant cross-links that are reversible and break down under conditions that the composite polymer will experience during dilution. Polymers bearing hydroxyl groups are particularly suitable in this regard because it is well known that such polymers form complexes with boron containing salt such as borax in alkaline media. These complexes break down on dilution thus providing a convenient means of reversible cross-linking. Examples of hydroxyl bearing polymers are polyvinyl alcohol and its copolymers with vinyl acetate, certain polysaccharide and modified polysaccharides such as hydroxyethyl cellulose and methyl cellulose. Various proteins are yet another type of polymer knows to form reversible cross-links with appropriate cross-linking agents such as tannic acid, trichloroacetic acid and ammonium sulfate. Indeed such reactions are well known in the art and widely used in protein purification. Still another class of polymers that can be reversibly cross-linked are those bearing charged groups, particularly carboxyl. These polymers can be cross-linked with metal ions such as zinc and calcium. Examples of polymers falling into this class are acrylic polymers such as polyacrylic acid, polymethacrylic acids and copolymers with their various esters. Maleic acid containing polymers such as copolymers of maleic acid with methyl or ethyl vinyl ether are examples of such polymers.

From the discussion above, it is clear that a variety of hydrophilic polymers have potential utility as the water soluble component of the composite polymers disclosed herein. The key is to select an appropriate hydrophilic polymer that would be essentially insoluble in the composition (preferably a concentrated liquid system) under the prevailing electrolyte concentration, yet would dissolve or disperse when this composition is diluted under conditions of use. The tailoring of such polar polymers is well within the scope of those skilled in the art once the general requirements are known and the principle set forth.

By dissolving or dispersing under dilution is meant release of sufficient entrapped sensitive ingredient to ensure required performance. Generally, such performance is defined as the entrapped material performing at least 60% as efficiently as if it were not trapped.

An especially preferred water-soluble polymer used for the composite polymer is a partially hydrolyzed (i.e., hydrolyzed less than 100%) polyvinyl alcohol (PVA) with a percent hydrolysis of less than 95%, preferably lower than 90% and having a weight average molecular weight of less than 50,000, preferably less than 30,000.

It should be understood that the hydrophilic component of the composite polymer may be formed from one or more hydrophilic groups in the aqueous phase.

The monomer or mixture of monomers used which will form the hydrophobic core particles of the composite polymer (to which the hydrophilic polymer or polymers may or may not be chemically attached) used in the polymer system may be any emulsion polymerizable monomer that contains ethylenically unsaturated group such as styrene, α-methylstyrene, divinylbenzene, vinylacetate, acrylamide or methacrylamide and their derivatives, acrylic acid or methacrylic acid and their ester derivatives (e.g. butyl acrylate or methyl methacrylate). As noted, mixtures of these monomers are also useful.

It should be noted that these compounds are emulsion polymerizable monomers, not hydrophobic polymers.

The ratio of hydrophobic polymer core to hydrophilic water-soluble polymer can be in the range of 2:8 to 7:3 and preferably in the range of 4:6 to 6:4 by weight. The film properties derived from this emulsion can be manipulated either by the ratio of hydrophobic core to water-soluble polymer shell by the composition of the emulsion polymer or by the composition of the water soluble polymer.

A variety of techniques well known in the art can be used to prepare the composite polymer useful in the present invention. These include batch, semi-continuous and seeded polymerizations (Encyclopedia of Polymer Science and Engineering; V6). A particularly useful process is the semi-continuous batch process disclosed for example in U.S. Pat. No. 3,431,226.

Macro and microcapsules employing the novel composite polymer of the current invention can be fabricated by a variety of processes well known in the art. These include spray-on coatings employing either pan coaters or fluid bed coaters as taught in U.S. Pat. Nos. 3,247,014 and 2,648,609; spray drying as taught in U.S. Pat. Nos. 3,202,371 and 4,276,312; or various coacervation based techniques. A particularly convenient and simple process is spray drying. Here the payload (e.g. enzyme(s)), polymer and additional optional agents such as incipient cross-linkers or enzyme stabilizers are first combined with water and mixed well. The mixture is atomized by being pumped through the nozzle of a spray drier of desired opening into a heated drying chamber. The resulting fine powder microcapsules can be applied as is or go through further conditioning steps as required.

The particle size of the capsule should be less than 250 microns, preferably less than 100, more preferably 0.1 to 60 microns.

As indicated above, the hydrophilic water soluble polymer or polymers attaches to the hydrophobic core particles either chemically and/or physically. Chemical attachment occurs during polymerization through chemical bonding of a portion of the hydrophobic polymer to the hydrophilic core particles. The hydrophilic and hydrophobic segments may also bind via the interaction of, for example, Van der Waal forces. Alternatively, the hydrophilic molecules may physically entangle in a loose web surrounding the hydrophobic core particles.

While not wishing to be bound by theory, it is believed that some hydrophilic polymer or polymers chemically react with hydrophobic core particles while others cross-link with each other and together they form a sort of web or gel-like sieve with each other and enzyme or other sensitive components are trapped within.

It is further believed that this "sieve" serves to slow the migration of enzyme out of the capsule (i.e., capsule formed by the hydrophilic group attached to the core particles) while simultaneously slowing entry of formulation ingredients from outside into the capsule. Thus the emulsion polymer capsule protects the sensitive components "floating" in the sieve within.

This polymer capsule is particularly useful for encapsulation of detergent sensitive active ingredients such as one or more enzymes, perfumes, fluorescers and the like. The enzyme or enzymes can be encapsulated with this type of polymer simply by spray drying a mixture of enzyme or enzymes and this emulsion polymer. A variety of enzymes can be incorporated for use in liquid laundry detergents. These include lipases, cellulases, amylases, oxidases, and the like as well as combinations of these enzymes. Enzymes which are suitable for the current applications are discussed in EP Patent 0,286,773 A2 and U.S. Pat. No. 4,908,150.

The amount of enzyme or enzymes in the capsule may range from about 0.5 to 50%, more preferably 0.5 to 30% and most preferably 1% to 25% by weight.

It is often useful to incorporate into the capsule composition ingredients that help stabilize the enzyme to small amounts of water, alkali or other destabilizing components which enter the microcapsule during storage. A variety of suitable enzyme stabilizers can be employed inside the capsule (in addition to any stabilizer which may desirably be added to the composition itself). These include calcium salts such as $CaCl_2$; short chain carboxylic acids or salts therefore, such as formic acid, propionic acid, calcium acetate, or calcium propionate; polyethylene glycols; various polyols; and large molecules, such as specific hydrolyzed proteins. Examples of suitable enzyme stabilizers are disclosed in U.S. Pat. Nos. 4,518,694; 4,908,150 and 4,011,169, all of which are incorporated herein by reference. Generally enzyme stabilizer comprises 0.01–5% of the detergent composition. In general, less stabilizer is required when used inside the capsule than when stabilizer is used outside the capsule.

One interesting aspect of the invention is that, since the polymer of the invention is a composite polymer having hydrophilic molecules attached to hydrophobic cores and, in effect, forming a sort of web or mesh over the entrapped material (e.g., enzyme or enzymes), one might expect that smaller molecules (e.g., smaller enzyme stabilizers such as calcium acetate) would diffuse out of the "web" and be a much less effective stabilizer than a large molecule (e.g., cationic protein stabilizer) which cannot readily diffuse out. Unexpectedly, however, it has been discovered that both large and small stabilizer molecules may provide equal stabilization benefits (depending at least in part on selection of enzymes) when used inside the encapsulation polymer.

By large molecules are generally meant those having a molecular weight of greater than about 10,000 g/mole and by small molecules are generally meant those having a molecular weight less than about 500 g/mole. While not wanting to be bound by theory, this seems to illustrate that despite diffusion effects, the capsule is successfully retaining the desired components inside until release or dilution.

Another aspect of the invention is that the use of enzyme stabilizers within the capsule allows the use of much less stabilizer (up to an order of magnitude less) than if the stabilizer were used outside the capsule instead. Further, the use of less stabilizer is realized without sacrifice in detergency performance. Thus, a tremendous and unexpected stabilization boost is apparently provided merely by moving the stabilizer material inside the capsules of the invention. It should be understood by those skilled in the art that stabilizer may be used inside the capsule, outside the capsule or both inside and outside the capsule.

When the capsule is present in a concentrate, the protected component inside the capsule is released when the concentrate is diluted in water by the wash.

By concentrate is meant a composition having, in addition to other components, no more than 60%, by wt. water, preferably no more than 50% water.

If used in a dilute composition (e.g., detergent composition), although the water content of the detergent compositions is not critical and can range from about 10% to about 80%, it should preferably be formulated to contain an appropriate level of an agent which can render the water soluble polymers insoluble. The agent may be an electrolyte or a cross-link agent so that the capsules are stable structures in the liquid detergent composition but disintegrate when the detergent is diluted to a concentration of a wash solution (typically between 0.5–6 gm. of detergent formulation per liter of water).

The electrolyte may be mono-, di-, tri-, or tetravalent water soluble electrolyte which salts the water soluble polymer out of solution. Examples include sodium and potassium chloride, calcium and magnesium chloride, sodium and potassium sulfate, sodium citrate, sodium carbonate, sodium phosphates. Still other electrolytes are the low molecular weight polycarboxylates such as oxydisuccinate, tartrate mono and/or disuccinate, carboxymethyl oxysuccinate and the like.

Cross-linking agents highly suitable for the current invention are the various borate salts such as sodium, potassium borate and the complex borates such as borax. These materials are well known in the art to form reversible complexes with polyhydric alcohols such as PVA, dextrin etc. Of course other cross-linking agents which form reversible multivalent complexes with polyhydric alcohols can also be employed provided the complexes have sufficient stability.

The level of electrolyte and/or cross-linking agents required in the formulation depends on the composition of the capsules as well as the conditioning or finishing steps which the capsules may have undergone. For example, in some cases it may be advantageous to incorporate the agent directly into the capsule formulation prior to spray drying. In other cases the capsule may be soaked in a conditioning fluid that contains an agent in order to harden the capsule before incorporation in the HDL. Still in other cases, the capsule can be sprayed with such a "hardening" solution. The level of agent in the formulation should be sufficient to insure that the capsule remains intact in the heavy duty liquid detergent composition. Generally this amount ranges from between 0.1 to about 20%; preferably 1%–20% by weight based on the weight of the formulation. By intact is meant that the capsule will not dissolve in the formulation

Enzymes

The composite polymers found in the polymer system are designed to protect components which might be destroyed in solution outside the capsule. One such component might be one or more enzymes. These enzymes are described in greater detail below.

If a lipase is used, the lipolytic enzyme may be either a fungal lipase producible by *Humicola lanuginosa* and *Thermomyces lanuginosus,* or a bacterial lipase which show a positive immunological cross-reaction with the antibody of the lipase produced by the microorganism *Chromobacter viscosum* var. lipolyticum NRRL B-3673. This microorganism has been described in Dutch patent specification 154,269 of Toyo Jozo Kabushiki Kaisha and has been deposited with the Fermentation Research Institute, Agency of Industrial Science and Technology, Ministry of International Trade and Industry, Tokyo, Japan, and added to the permanent collection under nr. KO Hatsu Ken Kin Ki 137 and is available to the public at the United States Department of Agriculture, Agricultural Research Service, Northern Utilization and Development Division at Peoria, Ill., USA, under the nr. NRRL B-3673. The lipase produced by this microorganism is commercially available from Toyo Jozo Co., Tagata, Japan, hereafter referred to as "TJ lipase". These bacterial lipases should show a positive immunological cross-reaction with the TJ lipase antibody, using the standard and well-known immunodiffusion procedure according to Ouchterlony (Acta. Med. Scan., 133, pages 76–79 (1950).

The preparation of the antiserum is carried out as follows:

Equal volumes of 0.1 mg/ml antigen and of Freund's adjuvant (complete or incomplete) are mixed until an emulsion is obtained. Two female rabbits are injected with 2 ml samples of the emulsion according to the following scheme:

day 0: antigen in complete Freund's adjuvant
day 4: antigen in complete Freund's adjuvant
day 32: antigen in incomplete Freund's adjuvant
day 60: booster of antigen in incomplete Freund's adjuvant The serum containing the required antibody is prepared by centrifugation of clotted blood, taken on day 67.

The titre of the anti-TJ-lipase antiserum is determined by the inspection of precipitation of serial dilutions of antigen and antiserum according to the Ouchterlony procedure. A $2^5$ dilution of antiserum was the dilution that still gave a visible precipitation with an antigen concentration of 0.1 mg/ml.

All bacterial lipases showing a positive immunological cross-reaction with the TJ-lipase antibody as hereabove described are lipases suitable in this embodiment of the invention. Typical examples thereof are the lipase ex *Pseudomonas fluorescens* IAM 1057 available from Amano Pharmaceutical Co., Nagoya, Japan, under the trade-name Amano-P lipase, the lipase ex *Pseudomonas fragi* FERM P 1339 (available under the trade-name Amano-B), the lipase ex *Pseudomonas nitroreducens* var. lipolyticum FERM P1338, the lipase ex Pseudomonas sp. available under the trade-name Amano CES, the lipase ex *Pseudomonas cepacia,* lipases ex *Chromobacter viscosum,* e.g. *Chromobacter viscosum* var. lipolyticum NRRL B-3673, commercially available from Toyo Jozo Co., Tagata, Japan; and further Chromobacter viscosum lipases from U.S. Biochemical Corp. USA and Diosynth Co., The Netherlands, and lipases ex *Pseudomonas gladioli.*

An example of a fungal lipase as defined above is the lipase ex *Humicola lanuginosa,* available from Amano under the tradename Amano CE; the lipase ex *Humicola lanuginosa* as described in the aforesaid European Patent Application 0,258,068 (NOVO), as well as the lipase obtained by cloning the gene from *Humicola lanuginosa* and expressing this gene in *Aspergillus oryzae,* commercially available from NOVO industri A/S under the tradename "Lipolase". This lipolase is a preferred lipase for use in the present invention.

While various specific lipase enzymes have been described above, it is to be understood that any lipase which can confer the desired lipolytic activity to the composition may be used and the invention is not intended to be limited in any way by specific choice of lipase enzyme.

The lipases of this embodiment of the invention are included in the liquid detergent composition in such an amount that the final composition has a lipolytic enzyme activity of from 100 to 0,005 LU/ml in the wash cycle, preferably 25 to 0.05 LU/ml when the formulation is dosed at a level of about 0.1–10, more preferably 0.5–7, most preferably 1–2 g/liter.

A Lipase Unit (LU) is that amount of lipase which produces 1/μmol of titratable fatty acid per minute in a pH stat under the following conditions: temperature 30° C.; pH=9.0; substrate is an emulsion of 3.3 wt. % of olive oil and 3.3% gum arabic, in the presence of 13 mmol/l $Ca^{2+}$ and 20 mmol/l NaCl in 5 mmol/l Tris-buffer.

Naturally, mixtures of the above lipases can be used. The lipases can be used in their non-purified form or in a purified form, e.g. purified with the aid of well-known absorption methods, such as phenyl sepharose absorption techniques.

If a protease is used, the proteolytic enzyme can be of vegetable, animal or microorganism origin. Preferably, it is of the latter origin, which includes yeasts, fungi, molds and bacteria. Particularly preferred are bacterial subtilisin type proteases, obtained from e.g., particular strains of *B. subtilis* and *B licheniformis.* Example of suitable commercially available proteases are Alcalase, Savinase, Esperase, all of NOVO Industri a/S; Maxatase and Maxacal of Gist-Brocades; Kazusase of Showa Kenko; BPN and BPN' proteases and so on. The amount of proteolytic enzyme, included in the composition, ranges from 0.05–50,000 GU/mg., preferably 0.1 to 50 GU/mg., based on the final composition. Naturally, mixtures of different proteolytic enzymes may be used.

While various specific enzymes have been described above, it is to be understood that any protease which can confer the desired proteolytic activity to the composition may be used and this embodiment of the invention is not limited in any way be specific choice of proteolytic enzyme.

In addition to lipases or proteases, it is to be understood that other enzymes such as cellulases, oxidases, amylases, peroxidases, and the like which are well known in the art may also be used. The enzymes may be used together with cofactors required to promote enzyme activity, i.e. they may be used in enzyme systems, if required. It should also be understood that enzymes having mutations at various positions (e.g., enzymes engineered for performance and/or stability enhancement) are also contemplated by the invention. One example of an engineered commercially available enzyme is Durazym® from Novo.

Optional Ingredients

In addition to the enzymes mentioned above, a number of other optional ingredients may be used.

Alkalinity buffers which may be added to the compositions of the invention include monoethanolamine, triethanolamine, borax and the like.

Hydrotropes which may be added include ethanol, sodium xylene sulfonate, sodium cumene sulfonate and the like.

Other materials such as clays, particularly of the water-insoluble types, may be useful adjuncts in compositions in which the capsules of this invention are used. Particularly useful is bentonite. This material is primarily montmorillonite which is a hydrated aluminum silicate in which about 1/6th of the aluminum atoms may be replaced by magnesium atoms and with which varying amounts of hydrogen, sodium, potassium, calcium, etc. may be loosely combined. The bentonite in its more purified form (i.e. free from any grit, sand, etc.) suitable for detergents contains at least 50% montmorillonite and thus its cation exchange capacity is at least about 50 to 75 meq per 100 g of bentonite. Particularly preferred bentonites are the Wyoming or Western U.S. bentonites which have been sold as Thixo-jels 1, 2, 3 and 4 by Georgia Kaolin Co. These bentonites are known to soften textiles as described in British Patent No. 401,413 to Marriott and British Patent No. 461,221 to Marriott and Guam.

In addition, various other detergent additives or adjuvants may be present in the detergent product to give it additional desired properties, either of functional or aesthetic nature.

Improvements in the physical stability and anti-settling properties of the composition may be achieved by the addition of a small effective amount of an aluminum salt of a higher fatty acid, e.g., aluminum stearate, to the composition. The aluminum stearate stabilizing agent can be added in an amount of 0 to 3%, preferably 0.1 to 2.0% and more preferably 0.5 to 1.5%.

There also may be included in the formulation, minor amounts of soil suspending or anti-redeposition agents, e.g. polyvinyl alcohol, fatty amides, sodium carboxymethyl cellulose, hydroxy-propyl methyl cellulose. A preferred anti-redeposition agent is sodium carboxymethyl cellulose having a 2:1 ratio of CM/MC which is sold under the tradename Relatin DM 4050.

Optical brighteners for cotton, polyamide and polyester fabrics can be used. Suitable optical brighteners include Tinopal LMS-X, stilbene, triazole and benzidine sulfone compositions, especially sulfonated substituted triazinyl stilbene, sulfonated naphthotriazole stilbene, benzidene sulfone, etc., most preferred are stilbene and triazole combinations. A preferred brightener is Stilbene Brightener N4 which is a dimorpholine dianilino stilbene sulfonate.

Anti-foam agents, e.g. silicon compounds, such as Silicane L 7604, can also be added in small effective amounts.

Bactericides, e.g. tetrachlorosalicylanilide and hexachlorophene, fungicides, dyes, pigments (water dispersible), preservatives, e.g. formalin, ultraviolet absorbers, anti-yellowing agents, such as sodium carboxymethyl cellulose, pH modifiers and pH buffers, color safe bleaches, perfume and dyes and bluing agents such as Iragon Blue L2D, Detergent Blue 472/572 and ultramarine blue can be used.

Also, soil release polymers and cationic softening agents may be used.

Also, if structured liquids are used, high active level structured liquids tend to be viscous due to the large volume of lamellar phase which is induced by electrolytes (>6000 cp). In order to thin out these liquids so that they are acceptable for normal consumer use (<3000 cp), both excess electrolyte and materials such as polyacrylates and polyethylene glycols are used to reduce the water content of the lamellar phase, hence reducing phase volume and overall viscosity (osmotic compression). Generally, the polymer should be sufficiently hydrophilic (less than 5% hydrophobic groups) so as not to interact with the lamellar droplets and be of sufficient molecular weight (>2000) so as not to penetrate into the water layers within the droplets.

Another optional ingredient which may be used particularly in structured liquids, is a deflocculating polymer.

In general, a deflocculating polymer comprises a hydrophobic backbone and one or more hydrophobic side chains and allows, if desired, the incorporation of greater amounts of surfactants and/or electrolytes than would otherwise be compatible with the need for a stable, low-viscosity product as well as the incorporation, if desired, of greater amounts of other ingredients to which lamellar dispersions are highly stability-sensitive.

The hydrophilic backbone generally is a linear, branched or highly cross-linked molecular composition containing one or more types of relatively hydrophobic monomer units where monomers preferably are sufficiently soluble to form at least a 1% by weight solution when dissolved in water. The only limitations to the structure of the hydrophilic backbone are that they be suitable for incorporation in an active-structured aqueous liquid composition and that a polymer corresponding to the hydrophilic backbone made from the backbone monomeric constituents is relatively water soluble (solubility in water at ambient temperature and at pH of 3.0 to 12.5 is preferably more than 1 g/l). The hydrophilic backbone is also preferably predominantly linear, e.g., the main chain of backbone constitutes at least 50% by weight, preferably more than 75%, most preferably more than 90% by weight.

The hydrophilic backbone is composed of monomer units selected from a variety of units available for polymer preparation and linked by any chemical links including —O—,

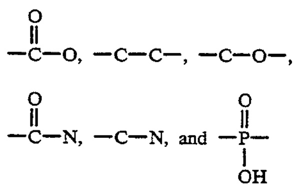

Preferably the hydrophobic side chains are part of a monomer unit which is incorporated in the polymer by copolymerizing hydrophobic monomers and the hydrophilic monomer making up the backbone. The hydrophobic side chains preferably include those which when isolated from their linkage are relatively water insoluble, i.e., preferably less than 1 g/l, more preferred less than 0.5 g/l, most preferred less than 0.1 g/l of the hydrophobic monomers, will dissolve in water at ambient temperature at pH of 3.0 to 12.5.

Preferably, the hydrophobic moieties are selected from siloxanes, saturated and unsaturated alkyl chains, e.g., having from 5 to 24 carbons, preferably 6 to 18, most preferred 8 to 16 carbons, and are optionally bonded to hydrophilic backbone via an alkoxylene or polyalkoxylene linkage, for example a polyethoxy, polypropoxy, or butyloxy (or mixtures of the same) linkage having from 1 to 50 alkoxylene groups. Alternatively, the hydrophobic side chain can be composed of relatively hydrophobic alkoxy groups, for example, butylene oxide and/or propylene oxide, in the absence of alkyl or alkenyl groups.

Monomer units which made up the hydrophilic backbone include:

(1) unsaturated, preferably mono-unsaturated, $C_{1-6}$ acids, ethers, alcohols, aldehydes, ketones or esters such as monomers of acrylic acid, methacrylic acid, maleic acid, vinyl-methyl ether, vinyl sulphonate or vinylalcohol obtained by hydrolysis of vinyl acetate, acrolein;

(2) cyclic units, unsaturated or comprising other groups capable of forming inter-monomer linkages, such as saccharides and glucosides, alkoxy units and maleic anhydride;

(3) glycerol or other saturated polyalcohols.

Monomeric units comprising both the hydrophilic backbone and hydrophobic sidechain may be substituted with groups such as amino, amine, amide, sulphonate, sulphate, phosphonate, phosphate, hydroxy, carboxyl and oxide groups.

The hydrophilic backbone is preferably composed of one or two monomer units but may contain three or more different types. The backbone may also contain small amounts of relatively hydrophilic units such as those derived from polymers having a solubility of less than 1 g/l in water provided the overall solubility of the polymer meets the requirements discussed above. Examples include polyvinyl acetate or polymethyl methacrylate.

The deflocculating polymer of the invention is described in greater detail in U.S. Pat. No. 5,147,576 to Montague et al. hereby incorporated by reference into the subject application.

The deflocculating polymer generally will comprise, when used, from about 0.1 to about 5% of the composition, preferably 0.1 to about 2% and most preferably, about 0.5 to about 1.5%.

The list of optional ingredients above is not intended to be exhaustive and other optional ingredients which may not be listed but which are well known in the art may also be included in the composition.

The viscosity of the present aqueous liquid detergent composition can be in the range of 50 to 20,000 centipoises, preferably 100 to 1,000 centipoises, but products of other suitable viscosities can also be useful. At the viscosities mentioned, the liquid detergent is a stable dispersion/emulsion and is easily pourable. The pH of the liquid detergent dispersion/emulsion which may range from 5 to 12.5, preferably 6 to 10.

More specifically, an ideal liquid detergent composition formulation for a non-structured liquid might be as follows:

| Ingredient | % by wt. |
|---|---|
| $C_{11.5}$ (Average) Alkyl Benzene Sulfonate | 8 to 12% |
| $C_{12}$-$C_{15}$ Alcohol Ethoxylate (9.E.O.) | 6 to 10% |
| Sodium Alcohol Ethoxysulfate | 4 to 8% |
| Sodium Citrate | 6 to 10% |
| Sodium Borate | 0 to 4% |
| Capsule Containing Composite Polymer Comprising Hydrophilic Polymer or Polymers Chemically and/or Physically Attached to Hydrophobic Core Particles and Enzyme Entrapped Within | 0.1 to 10% |
| Monoethanolamine | 1 to 4% |
| Triethanolamine | 1 to 4% |
| Detergent Adjuncts | 0.1 to 10% |
| Water | Balance to 100% |

In a composition in which it is desirable to maintain low initial pH which then rises in wash solution (i.e., pH "jump" solution such as is taught, for example, in U.S. Pat. No. 5,073,285 to Liberati et al., hereby incorporated by reference into the subject application) the monoethanolamine/triethanolamine buffer system is generally, although not necessarily, replaced by sorbitol and glycerol.

An example of a structured composition would be as set forth below.

| Ingredient | % by wt. |
|---|---|
| $C_{11.5}$ (Average) Alkyl Benzene Sulfonate | 8 to 30% |
| $C_{12}$-$C_{15}$ Alcohol Ethoxylate (9.E.O.) | 6 to 18% |
| Sodium Alcohol Ethoxysulfate | 0 to 8% |
| Sodium Citrate | 0 to 15% |
| Sodium Nitroacetate | 0 to 15% |
| Sodium Borate | 0 to 8% |
| Glycerol | 0 to 8% |
| Sorbitol | 0 to 15% |
| Capsule Containing Composite Polymer Comprising Hydrophilic Polymer or Polymers Chemically and/or Physically Attached to Hydrophobic Core Particles and Enzyme Entrapped Within. | 0.1 to 10% |
| Monoethanolamine | 0 to 4% |
| Triethanolamine | 0 to 4% |
| Decoupling Polymer (e.g., PPE 1067) | 0 to 2% |
| Detergent Adjuncts | 0.1 to 10% |
| Water | Balance to 100% |

EXAMPLES

The following examples are intended to further illustrate and describe the invention and are not intended to limit the invention in any way.

Example 1

Eight composite polymers were synthesized according to the recipes given in Table 1 below:

TABLE 1

(Example 1)
COMPOSITION AND PARTICLE SIZE OF COMPOSITE POLYMERS

| | Polymer | | | | | | | |
|---|---|---|---|---|---|---|---|---|
| | 1 | 2* | 3** | 4 | 5 | 6 | 7 | 8 |
| Deionized Water | 280 g | 280 g | 280 g | 280 g | 250 g | 280 g | 280 g | 250 g |
| Polyvinylalcohol | | | | | | | | |

TABLE 1-continued (Example 1)
COMPOSITION AND PARTICLE SIZE OF COMPOSITE POLYMERS

| | Polymer | | | | | | | |
|---|---|---|---|---|---|---|---|---|
| | 1 | 2* | 3** | 4 | 5 | 6 | 7 | 8 |
| 2,000 MW; 75% hydrolyzed | 50 g | — | — | — | — | 50 g | — | — |
| 13,000-23,000 MW; 78% hydrolyzed | — | 50 g | — | — | — | — | 50 g | — |
| 13,000-23,000 MW; 89% hydrolyzed | — | — | 50 g | — | — | — | — | — |
| 13,000-23,000 MW; 98% hydrolyzed | — | — | — | 50 g | — | — | — | — |
| 13,000-23,000 MW; 78% hydrolyzed | — | — | — | — | 30 g | — | — | — |
| Methylcellulose (15 cps) | — | — | — | — | — | — | — | 15 |
| Monomers | | | | | | | | |
| Styrene | 50 g | 50 g | 50 g | 50 g | 60 g | 30 | — | 15 |
| Butylacrylate | — | — | — | — | — | 20 | — | — |
| Vinyl acetate | — | — | — | — | — | — | 50 | |
| Particle Size | 80 nm | 80 nm | 116 nm | 184 nm | 90 nm | 85 nm | 64 nm | 438 nm |

*Amount of hydrophilic polymer attached to hydrophobic polymer particles was 49.1%.
**Amount of hydrophilic polymer attached to hydrophobic polymer particles was 50.1%.

The general procedure for synthesizing the polymers 1 to 7 of Table 1 is as follows: A half liter four-neck round bottom flask equipped with stirrer, condenser, nitrogen inlet and temperature controller was used for the polymerization reaction. Polyvinyl alcohol (PVA) and deionized water were charged to the reactor, and the reactor was heated and maintained at 75° C. to dissolve all the PVA under a slow stream of nitrogen. Six grams of monomer or monomer mixture was added to the reactor and emulsified for two minutes. 20 g of 1% potassium persulfate (initiator) solution was added to the reactor to start the emulsion polymerization reaction. The balance of the monomer or monomer mixture was metered into the reactor for a period of 30 to 35 minutes, and the reaction was held at 75° C. for another 30 minutes to complete the reaction. After the reaction, the emulsion was cooled to room temperature and the particle size was determined by Photon Correlation Spectoscopy using a Brookhaven B190 light scattering apparatus. The results are given in Table 1 above.

Polymer 8 containing methyl cellulose and polystyrene was prepared as follows: 15 grams of methyl cellulose (15 centipoise at 2% solution), 0.1 g of sodium bisulfate and 250 g of deionized water were added to a half liter four-neck round bottom flask equipped with stirrer, condenser, nitrogen inlet and temperature controller. The solution was stirred at room temperature to dissolve all the methyl cellulose under a slow stream of nitrogen. After dissolving all the methyl cellulose, the reactor was heated and maintained at 35° C. Five grams of styrene was added to the reactor and 20 grams of 1% potassium persulfate solution was added to start the polymerization reaction. Five minutes after adding the potassium persulfate solution, the balance of styrene monomer was metered to the reactor for 20 to 25 minutes and the reactor was held at 35° C. for another 40 minutes. After the reaction, the emulsion was cooled to room temperature.

Example 2

The 8 composite polymer compositions of Example 1 (set forth in Table I) were compared to 4 compositions comprising solely PVA (with varying levels of hydrolysis) to determine the sensitivity of the polymer films to salt.

To determine the properties of the various films, 2 g of the various polymer solutions were weighted into aluminum dishes and allowed to air dry for 4 days.

The solubility of the polymer films in sodium sulfate solution was determined by placing the polymer film in different sodium sulfate solutions ranging from 0–8% by wt. for 24 hours at room temperature. The solubility and film appearance were than recorded and summarized as set forth in Table II below:

TABLE 2

(Example 2)
SOLUBILITY OF POLYMER IN ELECTROLYTE SOLUTION

| | Visual assessment $Na_2SO_4$ Concentration | | | |
|---|---|---|---|---|
| Polymer Composition | 0% | 2% | 4% | 8% |
| Comparative 1 100% PVA; 2,000 MW; 75% hydrolyzed | 1 | 1 | 2 | 4 |
| Comparative 2 100% PVA; 13-23,000 MW; 78% hydrolyzed | 1 | 2 | 2 | 3 |
| Comparative 3 100% PVA; 13-23,000 MW; 89% hydrolyzed | 1 | 1 | 2 | 4 |
| Comparative 4 100% PVA; 13-23,000 MW; 98% hydrolyzed | 3 | 4 | 4 | 4 |
| Comparative 5 100% methylcellulose | 1 | 2 | 3 | 4 |
| Polymer 1, 50% PS, 50% PVA | 1 | 2 | 4 | 4 |
| Polymer 2, 50% PVA, 50% PS | 1 | 1 | 4 | 4 |
| Polymer 5, 33.3% PVA 66.7% PS | 2 | 3 | 4 | 4 |
| Polymer 3, 50% PVA, 50% PS | 1 | 2 | 4 | 4 |
| Polymer 4, 50% PVA, 50% PS | 4 | 4 | 4 | 4 |
| Polymer 8, 50% methylcellulose, 50% PS | 2 | 3 | 3 | 4 |

Score
1 - Film completely dissolve or disintegrates to submicron particles
2 - Film disintegrate to small pieces
3 - Film swell but remain intact
4 - Film did not change in appearance The results from Table II above demonstrate that highly hydrolyzed PVA (i.e., comparative 4 with 98% hydrolysis) is not suitable for encapsulation purposes since it will not break down in water at room temperature (i.e., had score of 3 at 0% electrolyte concentration). Partially hydrolyzed PVA can dissolve completely in water at room temperature, but requires very high electrolyte level (i.e., at least about 8%) to maintain film integrity. This can be seen from the fact that at both 2% and 4% salt concentrations the film formed with partially hydrolyzed PVA (comparative example 1-3) disintegrated to small pieces. In addition (as seen in Example 3 which follows), the partially hydrolyzed PVA tends to swell significantly in concentrated liquid detergents (i.e., 708% swelling for 78% hydrolyzed PVA compared to 230% swelling for the 98% hydrolyzed PVA).

The disadvantages of these polymers can be overcome by employing the composite polymers made by the methods described in this invention. Films derived from the emulsions prepared by polymerizing styrene in the presence of partially hydrolyzed PVA have good water resistance (i.e., well below the 708% swelling for partially hydrolyzed PVA not used in a composite copolymer—as seen in Example 3); as well as an excellent combination of salt sensitivity together with the ability to completely dissolve or disperse to submicron units water at room temperature.

This can be seen, for example, from polymer 1, which is clearly salt resistant at concentrations of 4% salt and readily disperses at 0% or in polymer 5 which has good salt resistance at concentrations of 2% and still readily disintegrates at 0% concentration.

Example 3

Polymers of the invention were compared to polymers comprising solely PVA to determine water resistance. As in Example 2, to determine film properties, 2 g of the polymer solutions were weighed into aluminum dishes and allowed to dry for four days.

Water resistance was determined by measuring the swellability of the film in a concentrated liquid detergent having the composition set forth below:

| CONCENTRATED LIQUID DETERGENT COMPOSITION | |
|---|---|
| Sodium alkylbenzenesulfonate | 9.8% |
| Alcohol Ethoxylate $C_{12-15}$ 9EO | 8.0% |
| Sodium Alcohol EO sulfate | 6.0% |
| Propylene glycol | 4.0% |
| Sodium Xylene Sulfonate | 3.0% |
| Sodium Borax Pentahydrate | 2.7% |
| Monoethanol amine | 2.0% |
| Triethanol amine | 2.0% |
| Sodium hydroxide (50%) | 1.8% |
| Water | 60.7% |

The film was placed in the concentrated liquid for 24 hours at room temperature. The weight of the swollen film was measured after the film was rinsed with deionized water and excess non absorbed water removed with a paper towel. The % swelling was calculated by dividing the weight of the swollen film by the weight of the non swollen film. The results are given in Table 3 below:

TABLE 3

| % SWELLING IN CONCENTRATED LIQUID DETERGENT | |
|---|---|
| Polymer Composition | % Swelling |
| 100% PVA 13-23,000 MW, 78% hydrolyzed (Comparative 2) | 708% |
| 100% PVA, 13-23,000 MW; 98% hydrolyzed (Comparative 4) | 230% |
| Polymer 2, 50% PVA, 50% PS (13-23K MW; 78% Hydrolyzed) | 455% |
| Polymer 5 33.3% PVA, 66.7% PS (13-23K MW; 78% hydrolyzed) | 203% |

TABLE 3-continued

| % SWELLING IN CONCENTRATED LIQUID DETERGENT | |
|---|---|
| Polymer Composition | % Swelling |
| Polymer 4, 50% PVA, 50% PS (13-23K MW; 98% hydrolyzed) | 158% |

As indicated above, these results show that partially hydrolyzed (78% hydrolyzed) PVA swells significantly. While the 98% hydrolyzed PVA is suitable in this regard, as seen in Example 2, such a polymer is deficient because it will not readily dissolve upon dilution (i.e., at 0% salt levels).

With regard to the composite polymers of the invention (polymers 2, 4, & 5), each of these shows significantly less swelling than the partially hydrolyzed (i.e., 78% hydrolyzed) 100% PVA polymer.

Tables 2 and 3 in Examples 2 & 3 also show that film properties can be manipulated merely by changing the ratio of polystyrene to PVA. Thus, while comparative example 2 (100% PVA), polymer 2 (50% PVA, S0% styrene) and polymer 5 (33.3% PVA, 67.7% styrene) differ only in ratios of PVA to styrene (i.e., all have 13-23 K MW and are 78% hydrolyzed), polymer 5 becomes insoluble at lower $Na_2SO_4$ levels than polymer 2 (i.e., provides salt resistance at even 2% salt levels) and both polymer 2 and polymer 5 become insoluble (i.e., to form insoluble capsules) much more effectively at lower electrolyte than comparative 2 (which disintegrates at levels of over 4% salt). Further, both polymers swell to much lesser extent than comparative 2 (i.e., 708% swelling of comparative versus 455% and 203% swelling, respectively, for polymers 2 and 5).

Example 4

Preparation of Enzyme Microcapsules

The composite emulsion polymers of Table 1 were used to encapsulate a lipase enzyme for incorporation into a concentrated liquid detergent formulation. A solution prepared by mixing 69 g of emulsion polymer (pH:6-8) and 37.5 g of Lipolase 100 L (ex. Novo) was spray dried at the following conditions using a Yamato Pulvis Mini Spray to give free flowing enzyme microcapsules with a particle size in the range of 1 to 30 micrometers.

| Spray Drying Condition | |
|---|---|
| Air inlet temperature | 100° C. |
| Air outlet temperature | 55° C. |
| Atomizing air pressure | 1.5 kgf/$cm^2$ |
| Solution feeding rate | 2.5 ml/minute |
| Spraying nozzle | Model 1650S |

The composition of the enzyme microcapsule is shown in the Table below:

| | % Polymer | % Lipolase 100 L |
|---|---|---|
| Capsule 1 | 64.8%* | 35.2% |
| Capsule 2 | 64.8%** | 35.2% |
| Capsule 3 | 64.8%*** | 35.2% |

*Polymer used was polymer 1 from Table 1 (i.e., 50-50 PVA/styrene wherein PVA has MW 2000 and 75% hydrolyzed)
**Polymer used was polymer 2 from Table 1 (i.e., 50-50 PVA/styrene wherein PVA has MW 13-23K & 78% hydrolyzed)
***Polymer used was polymer 3 from Table 1 (i.e., 50-50 PVA/styrene wherein PVA has MW 13-13K & 89% hydrolyzed)

Example 5

Enzyme Stability in Concentrated Liquid Detergent

Concentrated liquid detergents containing the enzyme microcapsules of Example 4 were prepared according to the formula shown in the Table below:

| COMPOSITION OF ENZYME-CONTAINING CONCENTRATED LIQUID DETERGENT | | | | |
|---|---|---|---|---|
| INGREDIENT | A | B | C | D |
| Alkyl Benzenesulfonic Acid | 27.3% | 27.3% | 27.3% | 27.3% |
| Alcohol Ethoxylated $C_{12-15}$ 9EO | 12.0% | 12.0% | < | < |
| Citric Acid | 7.1% | 7.1% | < | < |
| Sodium Borate | 2.7% | 2.7% | < | < |
| Glycerol | 5.0% | 5.0% | < | < |
| PPE 1067 (33%)* | 3.0% | 3.0% | < | < |
| Savinase 16 OL | 0.6% | 0.6% | < | < |
| NaOH (50%) | 14.4% | 14.4% | < | < |
| Ethanolamine | 2.0% | 2.0% | < | < |
| Triethanolamine | 2.0% | 2.0% | < | < |
| Water | 23.3% | 23.3% | < | < |
| Lipolase 100L | — | — | — | 0.6% |
| Enzyme Capsule 1 | 0.6% | — | — | — |
| Enzyme Capsule 2 | — | 0.6% | — | — |
| Enzyme Capsule 3 | — | — | 0.6% | — |

*Decoupling Polymer: Acrylic acid/lauryl methacrylate copolymer of MW about 5,000.

A comparative concentrated liquid detergent of the same formula was also prepared using non-encapsulated Lipolase 100L. These formulated concentrated liquid detergents were stored at 37° C. The stability of enzyme at 37° C. was followed by measuring the enzyme activity. The half life of enzymes is shown in the Table below:

| ENZYME STABILITY IN CONCENTRATED LIQUID DETERGENT | |
|---|---|
| Capsule | Half Life at 37° C. |
| Comparative - Lipolase 100L | 2 days |
| Capsule 1 of Example 4* | 129 days |
| Capsule 2 of Example 4** | 63 days |
| Capsule 3 of Example 4*** | 64 days |

*Polymer in capsule was 50-50 PVA/styrene wherein PVA has MW 2,000 and 75% hydrolyzed and capsule was 64.8% polymer and 35.2% Lipolase.
**Polymer in capsule was 50-50 PVA/styrene wherein PVA has 13-23K MW and was 78% hydrolyzed and capsule was 64.8% polymer and 35.2% Lipolase.
***Polymer in capsule was 50-50 PVA/styrene wherein PVA has 13-23K MW and was 89% hydrolyzed and capsule was 64.8% polymer and 35.2% Lipolase.

This example clearly shows that the polymers of the present invention provide high stability to the lipase. Furthermore, it is interesting to note that Capsule 1 and Capsule 2 are synthesized from polyvinyl alcohol of 2,000 MW/75% hydrolysis and 13,000–23,000 MW/78% hydrolysis. The prior art (EP 0,266,796 A1) has shown that such partially hydrolyzed materials are unsuitable as coating for enzymes and only hydrolysis of 90% and higher should be used. However, by grafting these polymers to the hydrophobic core particles as described in the subject invention, the resulting material becomes entirely suitable for enzyme encapsulation.

Example 6

Release of Enzyme in a Wash Condition

The release of the encapsulated enzyme in a wash condition was studied at 25° C. and 40° C. One gram of sample A of example four was added to one liter of water and the enzyme activity was measured at different times. The result is given in the table below. As noted, the enzyme was completely released within one minute at 40° C. and three minutes at 25° C.

| ENZYME RELEASE PROPERTY IN A WASH CONDITION | | |
|---|---|---|
| | LIPASE ACTIVITY (LU/ml BUFFER) | |
| TIME | 25° C. | 40° C. |
| 1 min. | 0.47 | 0.55 |
| 2 min. | 0.47 | 0.51 |
| 3 min. | 0.52 | 0.54 |
| 4 min. | 0.52 | 0.53 |
| 5 min. | 0.53 | 0.54 |
| 10 min. | 0.53 | 0.52 |
| 15 min. | 0.47 | 0.53 |

Example 7

Preparation of Microcapsule

Polymer 2 of Table 1 was used to encapsulate a protease enzyme for incorporation into a concentrated liquid detergent formulation. Capsule 4 was prepared by spray drying a solution containing 163 g of polymer 2 and 18.3 g of protease solution (ex. Maxacal) at 130° C. inlet air temperature, 65° C. air outlet temperature and 1.5 kgf/cm atomizing air pressure using a Yamato Pulvis Mini Spray. Capsule 5 was prepared by spray drying a solution containing 149 g of polymer 2, 0.2 g of calcium acetate, 3.9 g of glycerol and 18.3 g of protease solution (ex. Maxacal) at the same spray drying condition as Capsule 4.

Example 8

Enzyme Stability in Concentrated Liquid Detergent

Concentrated liquid detergents containing the enzyme capsules of Example 7 were prepared according to the formula shown in the Table below:

| Composition of Enzyme-Containing Concentrated Liquid Detergent | | | |
|---|---|---|---|
| Ingredient | A | B | C |
| Alkyl Benenesulfonic Acid | 27.3% | 27.3% | 27.3% |
| Alcohol Ethoxylated C12-15, 9EO | 12.0% | 12.0% | 12.0% |
| Citric Acid | 7.1% | 7.1% | 7.1% |
| Sodium Borate | 2.7% | 2.7% | 2.7% |
| PPE 1067 (33%)* | 3.0% | 3.0% | 3.0% |
| NaOH (50%) | 14.4% | 14.4% | 14.4% |
| Ethanolamine | 2.0% | 2.0% | 2.0% |
| Triethanolamine | 2.0% | 2.0% | 2.0% |
| Water | 27.7% | 27.7% | 28.3% |
| Protease Solution | — | — | 0.6% |
| Capsule 4 | 1.2% | — | — |
| Capsule 5 | — | 1.2% | — |

*Decoupling Polymer: Acrylic acid/lauryl methacrylate copolymer of MW about 5,000.

A comparative concentrated liquid detergent of the same formula was also prepared using non-encapsulated protease solution (ex. Maxacal). These formulated liquid detergents were stored at 37° C. The stability of enzyme at 37° C. was followed by measuring the enzyme activity. The half-life of enzyme (time at which 50% enzyme activity still remains) is shown in the Table below:

| Enzyme Stability In Concentrated Liquid Detergent | |
|---|---|
| Capsule | Half Life at 37° C. |
| Comparative - Protease (ex. Maxacal) | 4 days |
| Capsule 4 of Example 7 | 17 days |
| Capsule 5 of Example 7 | 28 days |

Example 9

Preparation of Enzyme Capsule

A solution prepared by mixing 145 g Polymer 3 of Table 1 and 75 g of Lipolase 100 L was spray dried at 120° C. inlet air temperature, 65° C. air outlet air temperature and 1.5 kgf/cm$^2$ atomizing air pressure using Yamato Pulvis Mini Spray. 32 g (72% yield) of free flowing capsule was obtained.

A comparative solution prepared by mixing 145 g of polyvinyl alcohol solution (23% solid, 89% hydrolyzed, 13,000/23,000 MW) and 71.5 g of Lipolase was spray dried at the same condition. Only 10 g (22.7% yield)) capsule was obtained and the capsule has a fiber-like structure.

Example 10

Preparation of Enzyme Capsule

A solution prepared by mixing 58.5 g Polymer 4 of Table 1 and 37.5 g of Lipolase 100 L was spray dried at 120° C. inlet air temperature, 65° C. air outlet temperature and 1.0 kgf/cm$^2$ using a Yamato Pulvis Mini Spray. 18.2 g (72%) of free-flowing capsule was obtained.

A comparative solution prepared by mixing 145 g polyvinyl alcohol solution (23% solid, 13,000/23,000 MW, 98% hydrolyzed) and 71.5 g of Lipolase 100 L was spray dried at the same condition. No free-flowing capsule was obtained. The spray dried polymer formed big aggregates with a fiber-like structure.

Example 11

A solution prepared by mixing 100 grams of polymer 8 and 21 grams of Lipolase 100 L was spray dried at 130° C. air inlet temperature and 70° C. air outlet temperature using Yamato Pulvis Mini Spray. 3.6 grams of free flowing enzyme capsule was obtained. A comparative solution prepared by mixing 100 g of 7% methyl cellulose solution and 15 g of Lipolase 100 L was spray dried at the same condition and only 0.4 grams of capsule was obtained.

Examples 9, 10 and 11 clearly shows that polymers of the present invention can dramatically enhance the yield of the spray dried capsule and also can provide more useful capsule than the water soluble polymer.

Example 12

Both large and small molecule stabilizers stabilize equally well when used inside detergent capsule Various capsules were made utilizing the polymer of polymer 2 (50% polystyrene—50% PVA) and different enzyme stabilizers. The capsules were prepared by spray drying a solution containing varying amounts of the polymer (as set forth in Table I below), 11.25 grams protease solution (ex. Maxacal) and varying amounts of the stabilizer (as also set forth in Table I) at 130° C. inlet air temperature, 65° C. air outlet temperature and 1.5 kgf/cm atomizing air pressure using a Yamato Pulvis Mini Spray. The capsule was used in Formulation A below.

TABLE 1

| Detergent Formulation | A | B |
|---|---|---|
| Alkyl benezenesulfonic acid | 27.3% | 27.3 |
| Alcohol ethoxylated $C_{12-15}$ 9EO | 12.0 | 12.0 |
| Citric Acid | 7.1 | 7.1 |
| Sodium Borate $10H_2O$ | 3.5 | 3.5 |
| PPE 1067 (33%) | 3.0 | 3.0 |
| NaOH (50%) | 13.9 | 13.9 |
| Ethanolamine | 2.0 | 2.0 |
| Triethanolamine | 2.0 | 2.0 |
| Water | 28.0 | 28.0 |
| Capsule | 1.2 | 0 |
| Maxacal MC1.3 | 0.0 | 0.6% |

Control formulation B was identical to A except that protease was included directly in the formulation rather than the capsule.

The composition fed to the spray drier is shown in Table II below and theoretical protease capsule composition is shown in Table III.

TABLE 2

Composition of Feed to Spray Drier

| Ingredient (g) | Samples a | b | c | d | e | f |
|---|---|---|---|---|---|---|
| Maxacal | 11.25 | 11.25 | 11.25 | 11.25 | 11.25 | 11.25 |
| Polymer | 92.4 | 83.2 | 84.0 | 84.0 | 84.0 | 84.0 |
| Glycerol | — | 2.4 | — | — | — | — |
| CaAcetate | — | 0.2 | — | — | — | 1.5 |
| Quat Pro E | — | — | 9.0 | — | — | — |
| Al 55 | — | — | — | 4.0 | — | — |
| NaPropionate | — | — | — | — | 2.25 | — |
| $H_2O$ | — | — | — | 5.0 | 6.75 | 7.5 |
| Capsule Yield (g) | 24.8 | 21.9 | 23.6 | 23.9 | 22.3 | 23.6 |

TABLE 3

Theoretical Protease Capsule Composition (%)

| Samples | a | b | c | d | e | f |
|---|---|---|---|---|---|---|
| Maxacal | 15 | 15 | 15 | 15 | 15 | 15 |
| Polymer | 85 | 76.6 | 77.5 | 77.5 | 77.5 | 80 |
| Glycerol | — | 8 | — | — | — | — |
| CaAcetate | — | 0.4 | — | — | — | 5 |
| Quat Pro | — | — | 7.5 | — | — | — |
| Al 55 | — | — | — | 7.5 | — | — |
| NaPropionate | — | — | — | — | 7.5 | — |

Results of the experiments are set forth below:

TABLE 4

The Effect of Stabilizer on Encapsulated Maxacal Stability

| Sample | Room Temperature Half-Life (Days) | 37° C. Half-Life (Days) |
|---|---|---|
| Control | 80 | 8 |
| a No Stabilizer | 144 | 17 |
| b Glycerol + CaAcetate | 200 | 30 |
| c Quat Pro E | 210 | 30 |
| d Al-55 | 250 | 30 |
| e NaPropionate | 190 | 40 |
| f CaAcetate | 178 | 40 |

Each of Quat Pro E and Al-55 are described in U.S. Pat. No. 5,073,292, which is hereby incorporated by reference into the subject application.

As can be readily seen, whether small or large size stabilizer molecules were used made no difference on stability (i.e., stability was equally good). These results show that, contrary to what might be expected (based on the expected diffusion of smaller molecules such as calcium acetate or sodium propionate), small molecule stabilizers stabilize just as effectively as the larger stabilizer molecules.

Example 13

When Encapsulated, Much Less Stabilizer is Required

Various enzyme stabilizers are required in the amounts indicated in the Table below to stabilize enzyme in detergents formulation. These required amounts are again taken from the amounts of the stabilizer used in compositions as taught in U.S. Pat. No. 5,073,292.

This was compared to the level of stabilizer required inside a capsule (capsule of Example 12) when 1.2% capsule is used in formulation and results are set forth in the table below:

TABLE 5

The Effect of Encapsulation on Required Level of Stabilizer Using 1.2% Capsules in the Formulation

| | In Formulation Wt. % of HDL | Encapsulated Wt. % of capsule | Wt. of HDL (when encapsulated) |
|---|---|---|---|
| Quat Pro E | 1 | 7.5 | 0.09 |
| AL-55 | 2 | 7.5 | 0.09 |
| NaPropionate | 5 | 7.5 | 0.09 |
| CaAcetate | 0.1 | 5 | 0.06 |
| Glycerol/Borax | 5.0/3.5 | | — |
| Glycerol/Ca | — | 8/0.4 | 0.10/0.005 |

In addition, the effect of encapsulation on performance of the protease is set forth below:

TABLE 6

The Effect of Encapsulation on Protease Performance

| Sample | Delta-Delta Reflectance (AS-10) |
|---|---|
| Maxacal Liquid | 10.2 |
| Maxacal Capsules | 10.0 |
| Savinase Liquid | 10.9 |
| Savinase Capsules | 10.3 |

As can be seen from the first table, the amount of enzyme stabilizer used in the capsule is an order of magnitude less than that used in full formulation. As can be further seen, the use of capsules had no detrimental effect on detergency performance as measured Terg-o-tometer wash of AS-10 monitor cloth and described by delta-delta reflectance units. This is a test that is used to determine detergency whenever delta reflectance is defined as difference in reflectance between the unwashed cloth and the washed cloth and delta-delta reflectance is the improvement with enzyme over formulation without enzyme.

Example 14

Effect of Glycerol

The effect of glycerol (both inside and outside the capsule) on encapsulated enzyme stability is set forth below:

| | 37° C. Half-Life (Days) HDL No Glycerol | HDL w/Glycerol |
|---|---|---|
| Protease liquid (Composition of Example 8C) | 10 | 37 |
| Encapsulated protease (Composition of Example 8A) | 24 | 59 |
| Encapsulated protease and glycerol (Composition of Example 8B) | 43 | |

This example shows that stabilizer can be used to enhance stabilization from inside the capsule (43 days versus 24 days) or from outside the capsule (59 days versus 24 days). It should be understood that stabilizer can also be added both inside and outside the capsule.

We claim:

1. A polymer capsule for use in a detergent composition comprising:

(a) one or more enzymes;

(b) a composite polymer which comprises (i) hydrophobic polymer core particles; and (ii) a hydrophilic water soluble polymer or polymers chemically or physically attached to the hydrophobic core particles; and (c) enzyme stabilizer;

wherein said hydrophilic polymer or polymers is not soluble in the detergent composition but is dissolved upon dilution of said composition with water and wherein said polymer is selected from the group consisting of synthetic nonionic water soluble polymers selected from the group consisting of polyvinyl alcohol, copolymers of polyvinyl alcohol and vinyl ester salts, polyvinyl pyrrolidone, copolymers of pyrrolidone with styrene and copolymers of pyrrolidone with vinyl ester salts; modified polysaccharides selected from the group consisting of cellulose acetate, alkyl cellulose and hydroxy alkyl cellulose; proteins and modified proteins; and acrylic polymers selected from the group consisting of polyacrylic acid, polymethacrylic acids and esters of salts acids;

wherein said hydrophobic polymer core particles are polymers derived from emulsion polymerizable monomers containing an ethylenically unsaturated group selected from the group consisting of styrene, methylstyrene, divinylbenzene, vinylacetate, esters of acrylic acid, esters of methacrylic acid, and mixtures of any of the monomers;

the ratio of said hydrophobic core particles to hydrophilic water soluble polymer being from about 2:8 to about 7:3;

wherein the enzyme is entrapped between the core particles and a web formed by said hydrophilic polymer or polymers;

wherein the enzyme stabilizer is added inside the capsule; and wherein said polymer capsule comprises 0.1 to 10% by weight of the composition.

2. A polymer capsule according to claim 1, wherein the polyvinyl alcohol has a percent hydrolysis less than 90% and a weight average molecular weight less than 50,000.

3. A polymer capsule according to claim 1, wherein the enzyme or enzymes is selected from the group consisting of protease, lipase, amylase, cellulase, oxidase and mixtures thereof.

* * * * *